United States Patent
Calzavara et al.

(10) Patent No.: US 10,527,514 B2
(45) Date of Patent: Jan. 7, 2020

(54) SYSTEM AND METHOD FOR REAL TIME REMOTE MEASUREMENT OF GEOMETRIC PARAMETERS OF A PIPELINE IN THE LAUNCH STEP, THROUGH SOUND WAVES

(71) Applicant: SAIPEM S.p.A., San Donato Milanese, Milan (IT)

(72) Inventors: Adriano Calzavara, Milan (IT); Giancarlo Bernasconi, Milan (IT); Massimo Signori, Milan (IT)

(73) Assignee: SAIPEM S.p.A., San Donato Milanese, Milan (IT)

( * ) Notice: Subject to any disclaimer, the term of this patent is extended or adjusted under 35 U.S.C. 154(b) by 0 days.

(21) Appl. No.: 15/576,166

(22) PCT Filed: May 20, 2016

(86) PCT No.: PCT/IB2016/052969
§ 371 (c)(1),
(2) Date: Nov. 21, 2017

(87) PCT Pub. No.: WO2016/185435
PCT Pub. Date: Nov. 24, 2016

(65) Prior Publication Data
US 2018/0172546 A1 Jun. 21, 2018

(30) Foreign Application Priority Data
May 21, 2015 (IT) .......................... 102015000016565

(51) Int. Cl.
*G01B 17/04* (2006.01)
*G01N 29/06* (2006.01)
(Continued)

(52) U.S. Cl.
CPC .............. *G01M 3/243* (2013.01); *F16L 1/20* (2013.01); *G01B 17/04* (2013.01); *G01B 17/08* (2013.01);
(Continued)

(58) Field of Classification Search
CPC ....... G01B 17/04; G01B 17/08; G01M 3/243; G01N 29/0618; G01N 29/4436;
(Continued)

(56) References Cited

U.S. PATENT DOCUMENTS

| 4,092,868 A | 6/1978 | Thompson et al. |
| 5,400,788 A | 3/1995 | Dias et al. |

(Continued)

FOREIGN PATENT DOCUMENTS

| DE | 199 15 203 C2 | 11/2000 |
| EP | 1 448 970 B1 | 5/2004 |

(Continued)

OTHER PUBLICATIONS

International Search Report and Written Opinion of the International Searching Authority for corresponding International Patent Application No. PCT/IB2016/052969 dated Aug. 29, 2016, 9 pages.

(Continued)

*Primary Examiner* — Jacques M Saint Surin
(74) *Attorney, Agent, or Firm* — Merchant & Gould P.C.

(57) ABSTRACT

A system and method remotely measure in real time through sound waves, geometric parameters of a pipeline in the launch step. An acoustic transceiver positioned in a pipeline includes an acoustic transmitter emitting an input acoustic signal into the pipeline, based on an electric pilot signal. An acoustic receiver detects the input acoustic signal and generates a first electric measurement signal, dependent on the input acoustic signal. The acoustic receiver receives an input return signal dependent on the input acoustic signal and on pipeline geometric parameters, and generates a second electric measurement signal based on the return acoustic signal. A control unit generates an electric pilot signal and connects to the acoustic transceiver and receives the first electric measurement signal and the second electric measurement signal. The control unit measures the geometric parameters of the pipeline based on the first and second electric measurement signals.

32 Claims, 8 Drawing Sheets

(51) Int. Cl.
*G01N 29/44* (2006.01)
*F16L 1/20* (2006.01)
*G01B 17/08* (2006.01)
*G01N 22/02* (2006.01)
*G01N 29/11* (2006.01)
*G01N 29/34* (2006.01)
*G01N 29/46* (2006.01)
*G01N 29/48* (2006.01)
*G01M 3/24* (2006.01)
*F16L 1/235* (2006.01)

(52) U.S. Cl.
CPC .............. *G01N 22/02* (2013.01); *G01N 29/06* (2013.01); *G01N 29/0618* (2013.01); *G01N 29/11* (2013.01); *G01N 29/34* (2013.01); *G01N 29/4436* (2013.01); *G01N 29/46* (2013.01); *G01N 29/48* (2013.01); *F16L 1/235* (2013.01); *G01N 2291/02854* (2013.01); *G01N 2291/101* (2013.01); *G01N 2291/102* (2013.01); *G01N 2291/2636* (2013.01)

(58) Field of Classification Search
CPC ........ G01N 29/34; G01N 29/11; G01N 29/06; G01N 22/02; G01N 29/46; G01N 29/48; G01N 2291/02854; G01N 2291/101; G01N 2291/102; F16L 1/20; F16L 1/235
USPC .......................................................... 73/584
See application file for complete search history.

(56) References Cited

U.S. PATENT DOCUMENTS

| | | | |
|---|---|---|---|
| 5,995,447 A | 11/1999 | Mandal et al. | |
| 6,208,586 B1 * | 3/2001 | Rorden | E21B 47/101 |
| | | | 181/105 |
| 6,547,435 B1 | 4/2003 | Grossing et al. | |
| 6,597,997 B2 * | 7/2003 | Tingley | G01N 22/02 |
| | | | 324/635 |
| 6,751,560 B1 | 6/2004 | Tingley et al. | |
| 8,511,404 B2 * | 8/2013 | Rasheed | E21B 10/32 |
| | | | 175/384 |
| 9,322,807 B2 * | 4/2016 | Lu | G01N 29/04 |
| 9,394,785 B2 * | 7/2016 | Goodwin | E21B 33/13 |
| 2003/0033879 A1 | 2/2003 | Adewumi et al. | |
| 2004/0216512 A1 * | 11/2004 | Kwun | G01N 29/07 |
| | | | 73/1.82 |
| 2005/0279168 A1 | 12/2005 | Bungenberg | |
| 2008/0163700 A1 * | 7/2008 | Huang | G01B 17/025 |
| | | | 73/861.25 |
| 2013/0081449 A1 | 4/2013 | Li et al. | |
| 2013/0286778 A1 | 10/2013 | Kisner et al. | |
| 2014/0022530 A1 | 1/2014 | Farhadiroushan et al. | |

FOREIGN PATENT DOCUMENTS

| | | |
|---|---|---|
| RU | 2081252 C1 | 6/1997 |
| WO | 93/04363 A2 | 3/1993 |
| WO | 98/43062 A1 | 10/1998 |
| WO | 2009/087342 A1 | 7/2009 |

OTHER PUBLICATIONS

Del Giudice, S. et al., "Acoustic Response of a Sinusoidally Perturbed Hard-Walled Duct", Hindawi Publishing Corpration, 2013: 1-6 (2013).
Morgan, E., "Experience with the Acoustic Ranger—A Sound Method for Tube Inspection", Materials Evaluation, 39: 926-930 (1981).
Papadopoulou, K. et al., "An evaluation of acoustic reflectometry for leakage and blockage detection", J. Mechanical Engineering Science, 222(C): 959-966 (2008).
Communication pursuant to Rule 114(2) EPC: Third Party Observations for corresponding European Patent Application No. 16733197.4 dated Aug. 27, 2018, 5 pages.
Russian Search Report for corresponding Russian Patent Application No. 2017139770/28(069136) dated Sep. 23, 2019, 2 pages.

* cited by examiner

SYSTEM AND METHOD FOR REAL TIME REMOTE MEASUREMENT OF GEOMETRIC PARAMETERS OF A PIPELINE IN THE LAUNCH STEP, THROUGH SOUND WAVES

This application is a National Stage Application of PCT/IB2016/052969, filed 20 May 2016, which claims benefit of Serial No. 102015000016565, filed 21 May 2015 in Italy and which applications are incorporated herein by reference. To the extent appropriate, a claim of priority is made to each of the above disclosed applications.

FIELD OF APPLICATION

The present invention relates to a system and corresponding method for real time remote measurement of geometric parameters of a pipeline in the launch step, through sound waves.

STATE OF THE ART

During the launch step of pipelines for underwater conduits, by means of a pipeline-laying ship 200 (as diagrammatically shown in FIG. 7), the integrity of the pipeline 2 itself must be ensured from the handling on the ship 200 to the final arrangement on the seabed.

However, various factors, including the welding operations on the ship 200, the passage on the supporting transit facilities of the pipelines aboard the ship 200, the curvature of the pipeline in the launch step, the contact with the seabed, and so on, may cause local deformations of the pipelines 2 which may develop into greater damage, e.g. local dents or buckles, with possible critical consequences during and after the steps of installation.

For this reason, monitoring the geometric parameters of a pipeline, by means of real time measurement, in the launch step is a very important aspect for the timely diagnostics of any anomalies.

The detection of such anomalies may activate the implementation of corrective actions during the laying campaign itself with apparent advantages.

The non-reliable detection or failure to detect such anomalies may cause costly incidents during laying and when the line is in service, such as for example the interruption of the supply of hydrocarbons or environmental decay.

Currently, a measurement instrument which is normally used to identify the presence of defects, such as dents or buckles, springs or excessive deformations, related to the launching of a pipeline, is the so-called "buckle detector" BK, i.e. a mechanical instrument consisting of a circular gauge fitted on a carriage connected to the ship by means of a metal cable 201, and of a load cell adapted to monitor the tension of the metal cable.

The carriage is kept in an appropriate span position so as to monitor the critical zones subject to the most strain, which thus show the most anomalies or geometry deformations.

The carriage moves relative to the pipeline in the launch thereof and provides an alarm on the presence of deformations which may obstruct its forward travel and which are detected as the increased tension of the metal cable.

In such known solutions, the choice of the gauge size is indicated in standards, as a function of the inner diameter of the pipeline to be monitored, or in project specifications. Some typical production defects of the pipeline, such as ovalization, misalignment or inner diameter variability, are factors which influence the monitoring reliability.

The use of a mechanical instrument, such as the "buckle detector" BK, is invasive and implies operative difficulties, risks and other drawbacks.

Firstly, such a mechanical instrument is very cumbersome, given the presence of the metal cable, the carriage and the load cell; furthermore, it must be always present in the pipeline and constantly monitored and managed during the laying operations.

Furthermore, the metal cable for the continuous connection between ship 200 and the "buckle detector" BK may reach a length of even hundreds of meters with the possibility of breakage due to the sliding inside the pipeline.

This influences the accuracy and reliability of the measurement.

Additionally, the launching, recovery and maintenance operations of the "buckle detector" BK (the latter operation being needed because of the mechanical wear caused by continuous operation) are highly time-consuming.

Furthermore, from the operative point of view, the "buckle detector" BK can detect a single anomaly in a single point with a low level of accuracy and repeatability of the measurement, with the risks of missed or false alarms.

Again, the use of a "buckle detector" BK may be risky because the following may occur during the operation of laying a pipeline: breakage of the metal cable; jamming of the "buckle detector" BK during the movement; one or more damages to the inner lining of the pipeline mainly caused by the passage of the metal cable. In light of these drawbacks, technical developments tends to prefer, where possible, the switch from an invasive approach (with the use of "buckle detector" BK) to a non-invasive approach.

In this regards, some systems are known on experimental level which detect anomalies in a pipeline by means of the non-intrusive transmission of radio-frequency (RF) electromagnetic waves in the pipeline itself (which operates as an electromagnetic waveguide).

The radio-frequency (RF) electromagnetic waves are transmitted by a launch source in an open end of the pipeline and the radio-frequency (RF) electromagnetic waves reflected by the inner walls of the pipelines are acquired by a processing unit. By implementing processing algorithms of the signal the processing unit estimates the presence of anomalies in the pipeline based on a comparison of the energy of the emitted signal and of the energy of the reflected signal.

Such a solution is used to obtain measurements with acceptable levels of accuracy, but has a limited applicability range in terms of distance (because of the attenuation to which the electromagnetic waves are subjected), i.e. has limits in the length of the pipeline stretch which can be monitored. These limits may be very penalizing in some situations.

Furthermore, in some situations, in which the electromagnetic waves are in the microwave field, reflected waves may be received deriving from a plurality of very small-sized defects which are negligible for monitoring purposes but which generate a non-negligible cumulative result on the overall received reflected wave and may even cause a sort of "self-jamming" of the electromagnetic receiver.

The need is thus felt to provide non-invasive monitoring and measuring systems capable of ensuring suitable precision in the detection of defects and anomalies (avoiding the aforesaid self-jamming phenomena at the same time) on long distances (thus capable of monitoring long stretches of pipeline), and also capable of determining the position, shape and geometric parameters of each detected defect with great accuracy.

In particular, the need is felt to identify defects and anomalies related to some relevant zones of the pipeline, e.g. with reference to i) contact zone of the pipeline with the seabed (TDP—Touch Down Point); ii) zones of the pipeline span with the most curvature; iii) exit zone of the pipeline from the ship, i.e. from the dedicated supporting structure ("stinger"); iv) contact zones between pipeline and supports (e.g. roller beds) arranged on the ship or along the "stinger". The relevant zones may be at distances in the order of hundreds of meters to kilometers from the head of the pipeline.

Furthermore, in the technical reference field, the need is strongly felt to detect even macroscopic obstacles possibly present in the pipeline and/or progressive wavefronts which may run in the pipelines, so as to intervene more promptly than currently possible.

SUMMARY OF THE INVENTION

It the object of the present invention to provide a system for real time remote measurement, through sound waves, i.e. by means of pressure waves which propagate in the fluid inside the pipeline, of geometric parameters of a pipeline in the launch step which allows to overcome at least partially the drawbacks described above with reference to the prior art, and to meet to the aforesaid needs particularly felt in the considered technical field.

It is a further object of the present invention a method for real time remote measurement, through sound waves, i.e. by means of pressure waves which propagate in the fluid inside the pipeline, of geometric parameters of a pipeline in the launch step, which method can be carried out by the aforesaid system.

Such an object is achieved by a system according to claim 1.

Further embodiments of such a system are defined in claims 2-22.

A method according to the invention is defined in claim 23.

Further embodiments of such a method are defined in claims 24-32.

BRIEF DESCRIPTION OF THE DRAWINGS

Further features and advantages of the system and corresponding method for real time remote measurement, through sound waves, i.e. by means of pressure waves which propagate in the fluid inside the pipeline, of geometric parameters of a pipeline in the launch step according to the present invention will become apparent from the following description of preferred embodiments shown by way of non-limiting example with reference to the accompanying drawings, in which.

DETAILED DESCRIPTION

Figure 1:
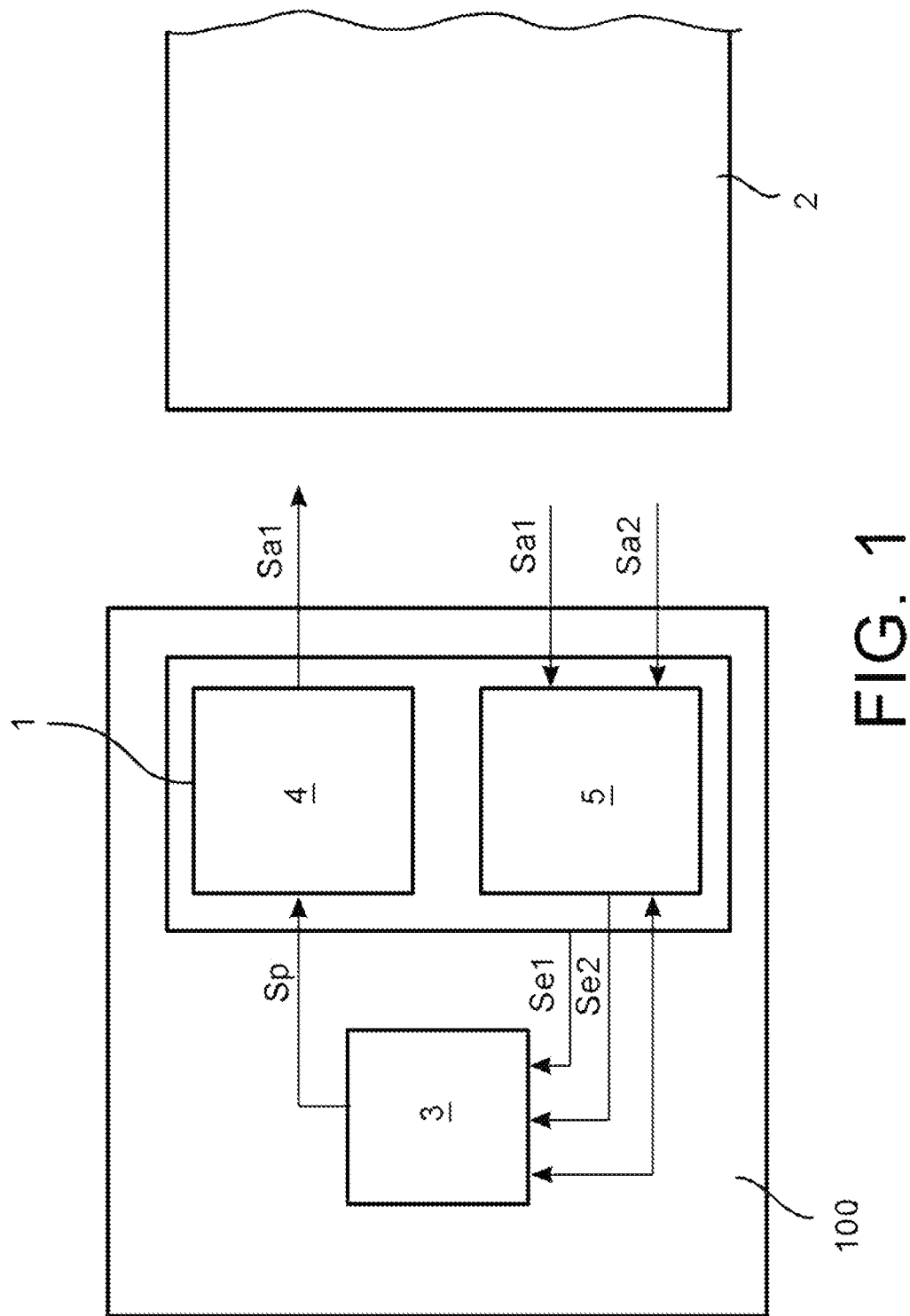
FIG. 1 shows a functional block chart of the system according to an embodiment of the invention.

A system for real time remote measurement, through sound waves, of geometric parameters of a pipeline in the launch step hereinafter also simply referred to as system, indicated as a whole by reference numeral 100, will be described below with reference to FIG. 1. Further detailed examples of the aforesaid geometric parameters will be disclosed below.

For the purposes of the present description, it is worth noting that acoustic waves mean pressure waves which propagate in the fluid inside the pipeline, e.g. at a minimum frequency of a few Hz and a maximum frequency depending, for example, on the diameter of the pipeline. For example, for a diameter of 4" (inches), i.e. about 10 cm, the maximum propagation frequency of an acoustic wave in the fluid of the pipeline is about 1,500 Hz, while for a diameter of 60" (inches), i.e. about 150 cm, the maximum propagation frequency of an acoustic wave in the fluid of the pipeline is about 100 Hz.

The system 100 comprises an acoustic transceiver unit 1, which can be positioned in a pipeline 2 (a portion of which is diagrammatically shown in FIG. 1), and a control unit 3.

The acoustic transceiver unit 1 comprises an acoustic transmission unit 4, configured to emit an input acoustic signal sa1 into the pipeline 2, based on an electric pilot signal sp.

The acoustic transceiver unit 1 further comprises an acoustic receiving unit 5, distinct from the acoustic transmission unit 4, configured to detect the input acoustic signal sa1 and to generate a first electric measurement signal se1, dependent on the input acoustic signal sa1.

The acoustic receiving unit 5 is further configured to receive an input return signal sa2, generated in the pipeline 2 and dependent on the input acoustic signal sa1 and on the geometric parameters of the pipeline, and to generate a second electric measurement signal se2 based on the return acoustic signal sa2.

The control unit 3 is configured to generate the electric pilot signal sp and is operatively connected to the acoustic transceiver unit 1 to provide the electric pilot signal sp and to receive the first electric measurement signal se1 and the second electric measurement signal se2.

Furthermore, the control unit 3 is configured to measure the geometric parameters of the pipeline 2 based on the first electric measurement signal se1 and on the second electric measurement signal se2.

It is worth noting that in the above-described system 100, the acoustic transmission unit 4 and the acoustic receiving unit 5 can work independently.

Furthermore, the control unit 3 can measure the geometric parameters of the pipeline 2 taking into account the acoustic return signal sa2 (e.g. generated by reflections/echoes in the pipeline 2) as well as the actual acoustic input signal sa1, which is accurately measured by the acoustic receiving unit 5 itself instead of being approximately estimated.

In other words, the acoustic receiving unit 5 measures both the acoustic input signal sa1 emitted by the acoustic transmission unit 4 and the acoustic return signal sa2.

The Applicant has indeed found that, by means of experiments, the exact knowledge of the acoustic input signal sa1 is a very important factor during the step of processing the echoes in order to obtain an accurate quantitative estimate of the defects.

It is worth noting that, in various examples of application, the geometric parameters of the pipeline 2 which may be measured by the system 100 include the section and/or the shape of the pipeline 2 (along the longitudinal development of the length of the pipeline 2 itself), e.g. the diameter of the pipeline which can be from about 4" (about 10 cm) to about 60" (about 150 cm), and/or defects or anomalies (e.g. dents or buckles) present along the pipeline 2, in any position.

In the case of defects or anomalies, the geometric parameters which can be measured with the present system 100 comprise the position, shape, and size of each detected defect or anomaly.

With regard to the positioning of the acoustic transceiver unit 1, it is worth noting that it may be inserted in any point inside the pipeline 2, but preferably in the first stretch of the pipeline 2, still arranged on the pipeline-laying ship 200, and more preferably in head of the pipeline 2 itself, where the head of the pipeline 2 means the termination of the pipeline 2 on the side of the pipeline-laying ship 200.

Figure 2:
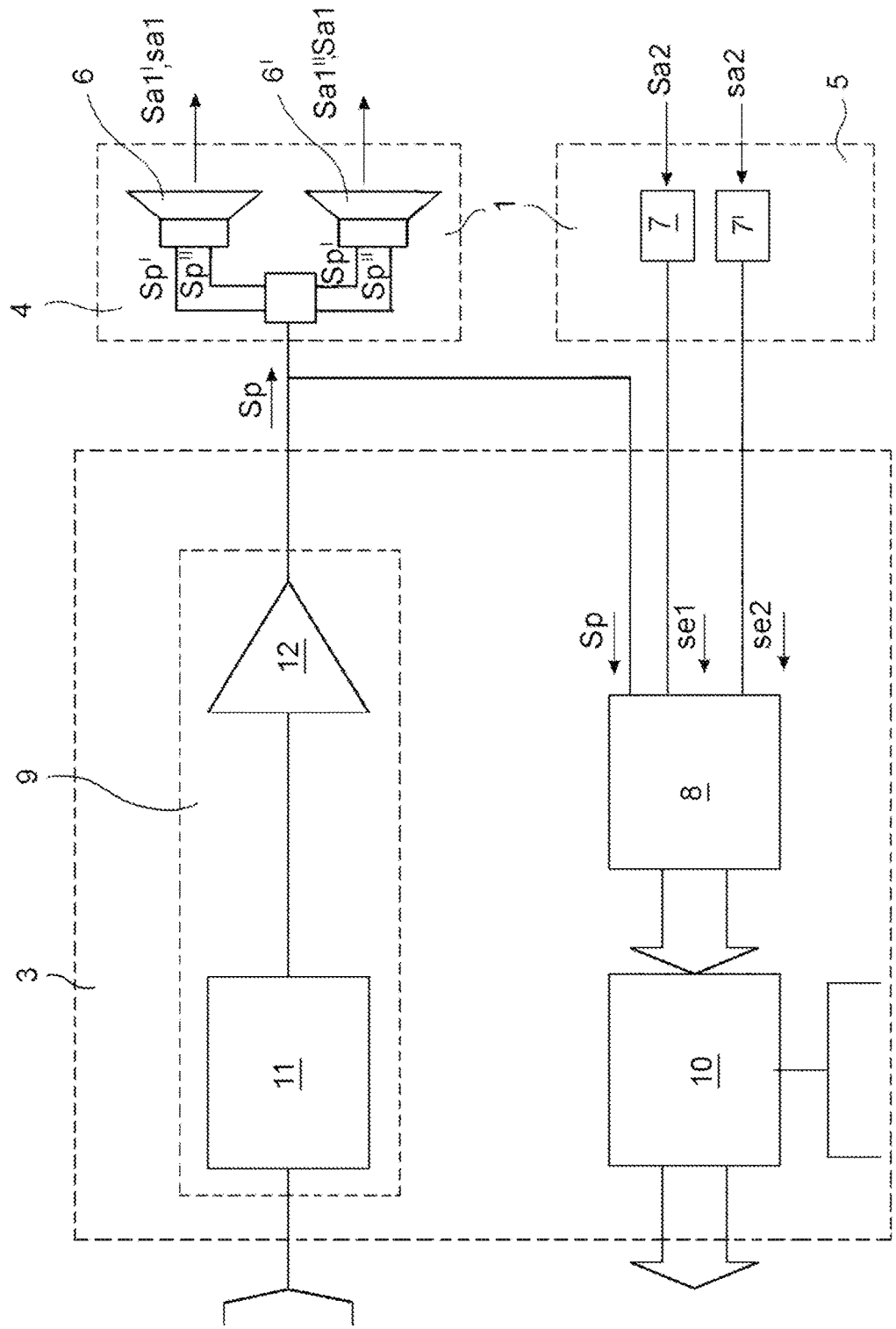
FIG. 2 shows a functional block chart of a further embodiment of the system.

According to a particular embodiment of the system, shown in FIG. 2, the acoustic transmission unit 4 comprises at least two acoustic transmission elements 6, 6' configured to emit an input acoustic signal sa1 comprising at least one mode of acoustic propagation.

In such a case, the control unit 3 is configured to generate an electric pilot signal sp comprising one or more electric pilot signals sp', sp" adapted to control each of the at least two acoustic transmission elements 6, 6'.

On the other hand, the acoustic receiving unit 5 comprises at least two acoustic receiving elements 7, 7' configured to receive an acoustic signal sa2 comprising the aforesaid at least one mode of acoustic propagation.

According to an optional embodiment, the aforesaid at least two acoustic transmission elements 6, 6' are configured to emit an input acoustic signal sa1 comprising the fundamental mode of acoustic propagation and at least one further mode of acoustic propagation.

Furthermore, in such a case, the aforesaid at least two acoustic receiving elements 7, 7' are configured to receive an acoustic signal sa2 comprising at least the fundamental mode of acoustic propagation and at least one further mode of acoustic propagation.

Advantageously, in such an option of implementation, a multiplicity of propagation modes may be generated, registered and identified (e.g. such as those shown in FIG. 3), each of which may be sensitive to various geometric parameters of the possible defects of the pipeline 2 (e.g. dents), thus allowing a greater robustness and a greater accuracy in identifying and reconstructing the type of anomaly.

For example, the fundamental acoustic mode (0,0) is symmetric to the axis of the pipeline 2 and is sensitive to changes of section, while mode (1,0) is anti-symmetric and thus capable of locating the position of a possible dent along the circumference of the pipeline 2; and so on.

According to a further optional embodiment, the aforesaid at least two acoustic transmission elements 6, 6' are configured to emit a first transmitted acoustic signal sa1' and a second transmitted acoustic signal sa1", which acoustically combine to form the input acoustic signal sa1.

According to a variant embodiment, the two acoustic transmission elements 6, 6' can be controlled independently from each other, so that the first transmitted acoustic signal sa1' and the second transmitted acoustic signal sa1" are different from each other, to determine a plurality of possible input acoustic signals.

Thereby, there are various degrees of freedom for generating acoustic input signals shaped and/or modulated in the most diverse manners, and adapted to the intended purposes.

For example, beats can be generated which modulate the input acoustic signal sa1.

According to an embodiment of the system, shown in FIG. 2, each of the aforesaid acoustic transmission units 4 or acoustic transmission element 6, 6' and each of the aforesaid acoustic receiving units 5 or acoustic receiving element 7, 7' comprises an electro-acoustic transducer, of type known per se.

Furthermore, the control unit 3 comprises an acquisition unit 8 of the first electric measurement signal se1 and of the second electric measurement signal se2, an electric pilot signal generating unit 9 and a processor 10.

The processor 10 is configured to carry out processing aimed at measuring the geometric parameters of the pipeline 2, based on the first electric measurement signal se1 and second electric measurement signal se2, and also to control the electric pilot signal generating unit 9.

The electric pilot signal generating unit 9, in a typical embodiment, comprises an electric signal generator 11, a modulator (implicitly included in the block 11) and an amplifier 12.

As will also be disclosed below, the electric signal generator 11 may be configured to generate a wide plurality of different signals and waveforms: e.g. waveforms with "chirp" (in particular, non-linear chirp), or Ricker waves, or Ormsby waves, or Klauder waves, and so on.

According to an embodiment of system 100, the acoustic transmission unit 4 comprises a matrix of loudspeakers, arranged in predetermined positions as acoustic transmission elements 6, 6'; the acoustic receiving unit 5 comprises a matrix of microphones, arranged in predetermined positions as acoustic receiving elements 7, 7'.

Figure 3:
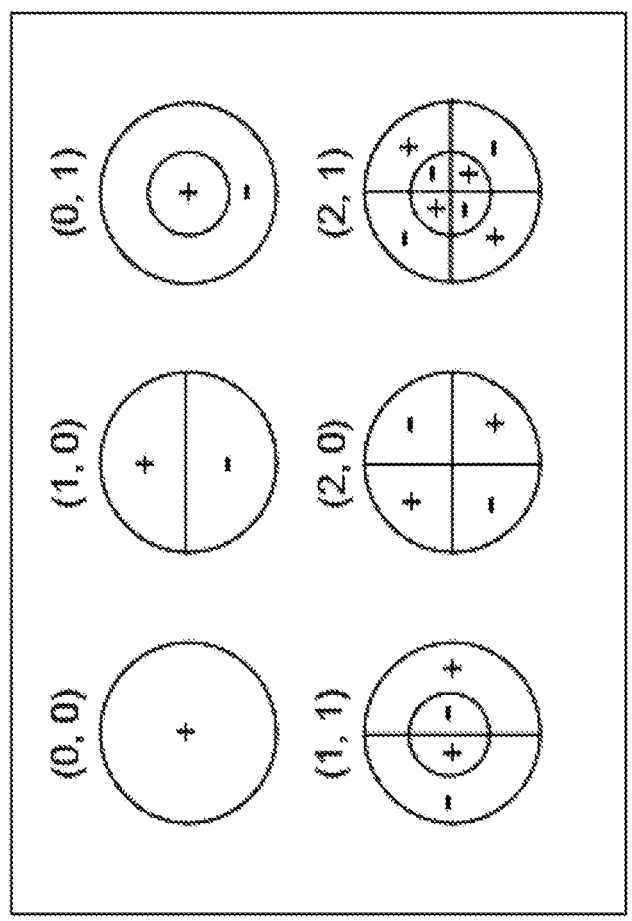
FIG. 3 shows some possible acoustic propagation modes in a cylindrical pipe.

According to different variants of embodiment, the number, geometric arrangement, position, reciprocal distances of the acoustic transmission elements and of the acoustic receiving elements may be the most different, according to the specific desired acoustic reception and transmission requirements and the requirements concerning the propagation modes to be reproduced (e.g. of those shown in FIG. 3).

Different examples of arrangement of acoustic transmission elements 6, 6' and of acoustic reception elements 7, 7', provided in different options of embodiment of the system, are shown in FIGS. 8a-8e.

As previously shown, the degrees of freedom offered by the presence of multiple acoustic emitters and receivers advantageously determine the possibility to manage acoustic signals comprising a multiplicity of propagation modes according to that desired in order to optimize the measurement accuracy and efficacy of the geometric parametric of the pipeline.

Furthermore, the matrix of transmission elements allows a more effective management of the emitted powers and also the possibility of generating complex waveforms by emitting different signals from each transmission element (e.g. to generate beats).

According to an embodiment of the system (which may also be provided autonomously with respect to the other embodiments disclosed in this description), the control unit 3 is configured to perform the following operations: defining an analysis waveform and generating the electric pilot signal sp so that the input acoustic signal sa1 is modulated by means of the defined analysis waveform; further defining an expected propagation model; thus, estimating an ideal acoustic return signal, based on the analysis waveform and the expected propagation model; then, carrying out a comparison between the estimated ideal acoustic return signal, within a time window, and the detected return acoustic signal sa2 based on the second electric measurement signal se2, within a corresponding time window; finally, obtaining the geometric parameters of the pipeline 2, based on the aforesaid comparison.

The geometric parameters thus obtained are representative of an actually detected shape of the pipeline 2 and of anomalies and/or defects found.

It is worth noting that the control unit 3 is configured to estimate the ideal return signal and to detect the return acoustic signal sa2 based on the aforesaid first and second electric measurement signals se1, se2.

According to an option of implementation, the control unit 3 is configured to define the analysis waveform based on a desired range of distances within which to detect defects, and/or based on a type of defects to be detected and/or based on an expected defect.

According to another optional embodiment, the system further comprises means for detecting background noise; in such a case, the control unit 3 is configured to define the analysis waveform by taking the detected background noise into account. Such a background noise may be an ambient noise present in the pipeline or an external ambient noise (e.g. coming from external machinery) which enters into the pipeline 2. In this regard, several variants are provided. For the internal ambient noise, the system 100 itself may be activated in advance with respect to the emission of the input acoustic signal sa1, so as to initially register the background noise; assuming that this noise is stationary, the sound emission is shaped in frequency to ensure an appropriate noise signal ratio on the entire concerned band.

For the external ambient noise, the means for detecting background noise are sound sensor of the known type, arranged outside the pipeline 2 (possibly near sources of ambient noise) and configured to register such external noise during the entire operative step. During the step of data processing, adaptive noise reduction techniques are used, which minimize the correlation between the external measurement and that inside the pipeline.

According to different variants of embodiment, the control unit 3 is configured to generate the analysis waveform as a sinusoidal waveform modulated in frequency by means of "chirp" and/or modulated in amplitude; or, in other variants, as a Ricker type wave or a Klauder type wave or an Ormsby type wave.

According to an optional embodiment, the control unit is configured to define the expected propagation model based on geometric parameters of a geometric model of the pipeline in the absence of laying anomalies.

According to a further optional embodiment, the control unit 3 is configured to define the expected propagation model also taking into account thermodynamic parameters of the fluid (e.g. air) contained in the pipeline, as will be disclosed below.

According to an embodiment, the control unit 3 is configured to carry out the aforesaid comparison by means of a cross-correlation between the estimated ideal acoustic return signal, within a time window, and the detected acoustic return signal sa2, within a corresponding time window.

Figure 5:
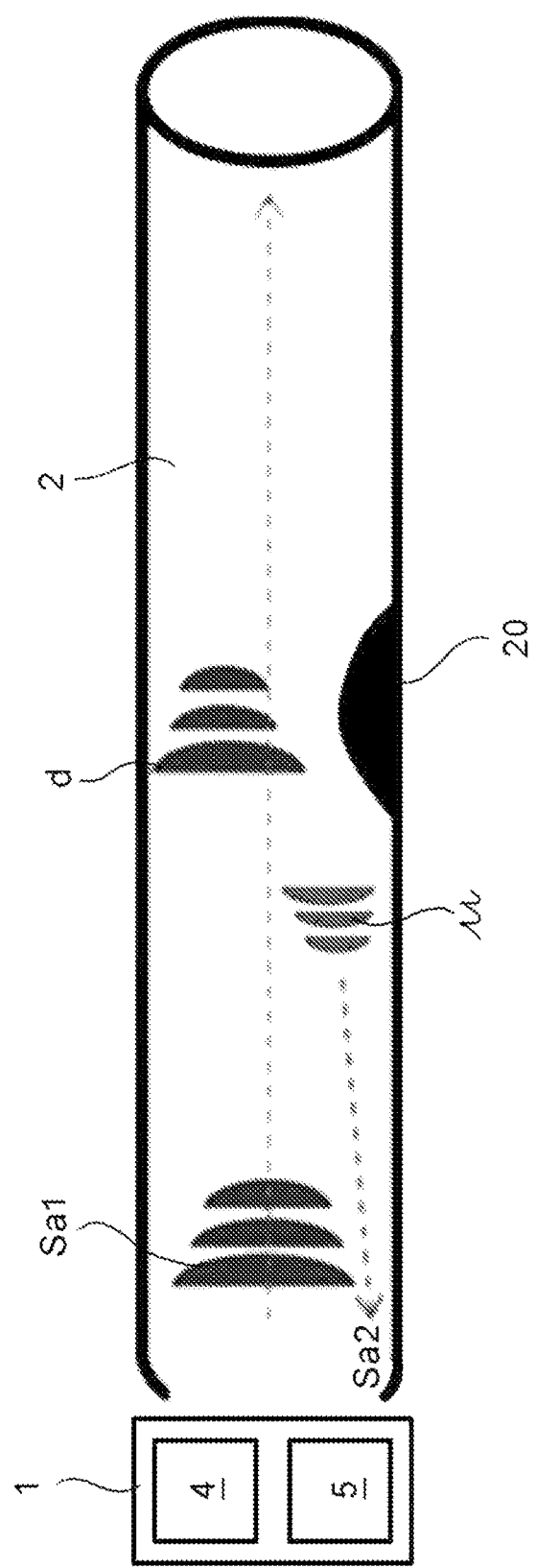
FIG. 5 diagrammatically shows a portion of the system and a cross section of a pipeline the defects of which can be detected by the system itself.

According to an optional embodiment, the control unit 3, in order to obtain the geometric parameters of the pipeline 2, is configured to carry out the following operations: determining a spatial reflection function of the pipeline, representative of reductions in diameter of the pipeline as a function of the distance based on the comparison between the estimated ideal acoustic return signal and the detected acoustic return signal sa2; then, identifying presence and spatial position of defects (e.g. 20 in FIG. 5) based on the aforesaid spatial reflection function; then, defining an estimated real geometric model of the pipeline, having an estimated defect at the identified defect position; furthermore, calculating an expected acoustic return signal, based on the estimated real geometric model of the pipeline; then, modifying geometric parameters of the estimated real geometric model of the pipeline 2, based on a cross-correlation between the expected acoustic return signal and the detected acoustic return signal sa2, within a time window corresponding to the position around the identified defect; finally, repeating the aforesaid modification process until there is a convergence of the aforesaid geometric parameters, to obtain a real geometric model of the pipeline 2 representative of the detected shape of the pipeline 2 and of the anomalies found.

Further details on the processing functionality of the control unit 3 will be described hereinafter by disclosing a method according to the invention.

According to an embodiment, the system 100 further comprises means for detecting the ambient pressure configured to supply the control unit 3 with information representative of the detected ambient pressure.

According to a further optional embodiment, the control unit 3 is configured to store temperature information and/or temperature profiles present or expected along the pipeline 2.

The control unit 3 is configured to define the expected propagation model and/or estimating the ideal return acoustic signal taking into account said ambient pressure and/or temperature information.

In such cases, the information relates to the pressure and temperature variations along the pipeline 2 are included in the propagation and the return acoustic signal estimate simulations. Since such pressure and temperature variations influence the wave propagation speed and the wave attenuation, the possibility of taking them into account allows to achieve a greater accuracy in the defect positioning and quantification, respectively.

According to an optional embodiment, the control unit 3 is configured to store a plurality of measurements of geometric parameters and to estimate a spatial-temporal evolution of one or more sections of the pipeline 2 based on said plurality of measurements.

According to another option of implementation, system 100 further comprises means for estimating the shape of the pipeline 2 in the launch step configured to measure the cross sections of portions of the pipeline in the launch step while still aboard the launching means and to provide information representative of the shape of the pipeline 2, in the launch step and before laying, to the control unit 3, based on the progressively measured cross sections.

In such a case, the control unit 3 is configured to measure the geometric parameters of the pipeline also taking into account the aforesaid information representative of the shape of the pipeline 2 in the launch step and still aboard a pipeline-laying naval vessel 200.

Figure 4A:
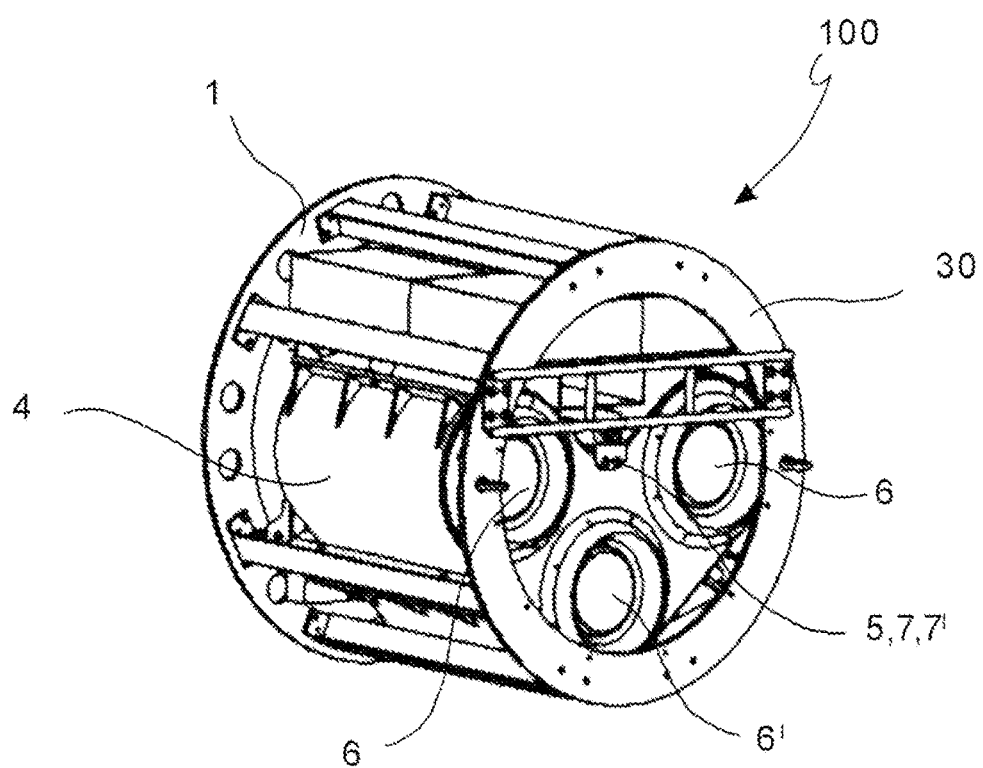
FIGS. 4A and 4B show a mechanical/structural conformation of a further embodiment of the system.
Figure 4B:
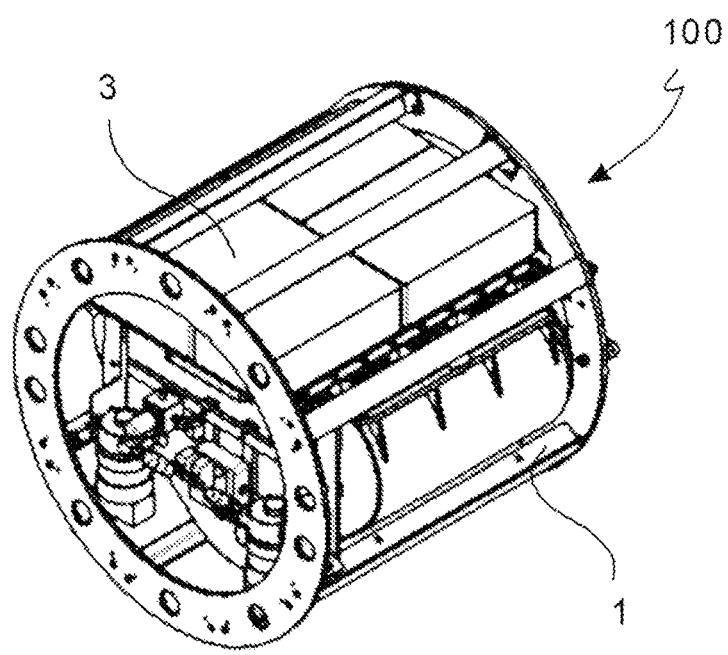

According to an embodiment of the system (shown in FIGS. 4A and 4B), the acoustic transceiver unit 1 can be mechanically integrated in a single module 30 to be applied to the inner clamp adapted to manage coupling and welding of portions of the pipeline 2 in the launch step and generally known as ILUC (Internal Line Up Clamp); the control unit 3 can be integrated in the same module 30.

In a variant embodiment, the control unit 3 can be arranged remotely with respect to the acoustic transceiver unit 1 and the system further comprises electronic communication means between the acoustic transceiver unit 1 and the control unit 3.

Hereinafter, a method will be described for real time remote measurement, through sound waves, i.e. pressure waves which propagate in the fluid in the pipeline (as previously defined), of geometric parameters of a pipeline in the launch step. Such a method can be executed by means of a system 100 such as the previously described one.

The method comprises the steps of emitting, into the pipeline 2, an input acoustic signal sa1, based on an electric pilot signal sp, by means of an acoustic transmission unit 4; thus, detecting the aforesaid input acoustic signal sa1, by means of an acoustic receiving unit 5, distinct from the acoustic transmission unit 4, and generating a first electric measurement signal se1, dependent on the input acoustic signal sa1. The method further provides for receiving, by means of the acoustic receiving unit 5, a return acoustic signal sa2, generated in the pipeline 2 and dependent on the input acoustic signal sa1 and on the geometric parameters of the pipeline 2, and generating a second electric measurement signal se2 based on the return acoustic signal sa2; finally, the step of measuring the geometric parameters of the pipeline 2, by means of a control unit 3, based on the first and second electric measurement signals (se1, se2, respectively).

According to an embodiment of the method, the step of emitting an input acoustic signal sa1 comprises emitting a first transmitted acoustic signal sa1', by means of a first element 6 of the acoustic transmission unit 4, and a second transmitted acoustic signal sa1", by means of a second element 6' of the acoustic transmission unit 5, respectively, in which the first transmitted acoustic signal sa1' and the second transmitted acoustic signal sa1" combine to form the input acoustic signal sa1.

According to an optional embodiment, the method comprises the further steps of defining an analysis waveform and generating the electric pilot signal sp so that the input acoustic signal sa1 is modulated by means of the defined analysis waveform; further defining an expected propagation model; then, estimating an ideal acoustic return signal, based on the analysis waveform and the expected propagation model; thus, carrying out a comparison between the estimated ideal acoustic return signal, within a time window, and the return acoustic signal sa2 detected based on the second electric measurement signal se2, within a corresponding time window, finally, obtaining the geometric parameters of the pipeline 2, based on the aforesaid comparison, in which the obtained geometric parameters are representative of a shape actually detected of the pipeline 2 and of anomalies and/or defects 20 found.

According to an optional embodiment, the step of defining the analysis waveform comprises defining the analysis waveform based on a desired range of distances within which to detect defects, and/or based on a type of defects to be detected and/or based on an expected defect.

According to an embodiment, the method further comprises the steps of detecting background noise and defining the analysis waveform taking into account the detected background noise.

According to a variant of embodiment, the step of generating the analysis waveform comprises generating a sinusoidal waveform modulated in frequency by means of "chirp" and/or modulated in amplitude and/or as a Ricker type wave or a Klauder type wave or an Ormsby type wave. According to another embodiment of the method, the step of defining the expected propagation model comprises defining the expected propagation model based on geometric parameters of a geometric model of the pipeline without laying anomalies and/or based on thermodynamic parameters of the fluid contained in the pipeline.

According to a further embodiment of the method, the step of carrying out a comparison comprises carrying out a cross-correlation between the estimated ideal acoustic return signal, within a time window, and the detected acoustic return signal sa2, within a corresponding time window.

According to an optional embodiment of the method, the step of obtaining the geometric parameters of the pipeline 2 comprises: determining, based on the comparison between the estimated ideal acoustic return signal and the detected acoustic return signal sa2, a spatial reflection function of the pipeline 2, representative of reductions in diameter of the pipeline as a function of the distance; thus, identifying presence and spatial position of defects 20 based on the aforesaid spatial reflection function; moreover, defining an estimated real geometric model of the pipeline 2, having an estimated defect at the identified defect position; then, calculating an expected acoustic return signal, based on the estimated real geometric model of the pipeline; thus, modifying geometric parameters of the estimated real geometric model of the pipeline, based on a cross-correlation between the expected acoustic return signal and the detected acoustic return signal sa2, within a time window corresponding to the position around the identified defect; finally repeating the aforesaid modification process until there is a convergence of the geometric parameters, to obtain a real geometric model of the pipeline representative of the detected shape of the pipeline 2 and of the anomalies found.

According to the various options of embodiment, the method is adapted to measure parameters relative to any combination of the following anomalies: geometric defects; dents; variations in section diameter; variations in section shape; blockages and/or obstacles present in the pipeline; significant discontinuities of the properties of the fluid contained in the pipeline; displacement of objects and/or defects in the pipeline between successive measurements; presence of water in the pipeline.

In an embodiment of the present invention, with reference again to the estimation and measurement algorithms of the geometric parameters of the pipeline, it is worth noting that a recognition technique of the acoustic signal reflected by a geometric anomaly of the pipeline (e.g. a dent 20) may be exploited. Advantageously, in this case, the input acoustic signal is provided so as to "interact" with the geometric anomaly of the pipe, so as to determine a reflected signal which contains, in its shape/amplitude as a whole as well as its energy, the information necessary and sufficient to reconstruct the concerned geometric parameters of the dent itself. In such a case, the availability of a matrix or array of elements 6, 6', in the acoustic transmission unit 5, connected to an arbitrary electric pilot signal generator 11, ensures a wide range of flexibility. In this regard, for example, the formulas known in literature (see for example: S. Del Giudice, G. Bernasconi "*Acoustic response of a sinusoidally perturbed hard walled duct*", Mathematical Problems in Engineering Volume 2013, Article ID 267291) are used, which formulas, with a formalism similar to that used to describe the Bragg effect, represent the bond between the shape of a dent (broken down as sum of sinusoidal dents along the pipe axis) and the amplitude and frequency content of the reflected acoustic signal. By combining such formulas with those which describe the attenuation of an acoustic signal propagating in a pipe (also known), it is possible to obtain the definition of an optimal emitted waveform (the aforesaid "analysis waveform"), i.e. a waveform capable of reaching a given distance (so that the total attenuation remains over a given threshold, e.g. over the sensitivity of the receiver) and to obtain information on the reflection caused by a possible dent, in a given case which can defined a priori (e.g. in a family of dents defined by the user), on all spatial sinusoidal components, frequency by frequency.

Thereby, the relationship which binds the dent to the reflected acoustic signal may be "inverted", to obtain the actual geometric parameters of the dent without ambiguity from the acoustic return signal (i.e. from the second electric measurement signal). For example, such an "inversion" may be performed by means of a Bayesian inversion according to the so-called "Tarantola's method". The inversion algorithm is stored and executed by the processor 10 of the control unit 3.

In such an embodiment, the method uses the observed parameter measurements to adapt the parameters of the physical model. Furthermore, the inversion algorithm uses a probabilistic flat wave acoustic propagation model characteristic for cylindrical pipes, with temperature calibration along the length of the pipeline to improve accuracy (taking into account the actual sound propagation speed). The "model space" represents the predictive physical model and is characterized by the parameters $\underline{m} = \{m_1, m_2, \ldots, m_M\}$; the "data space" represents measurable variables and is characterized by parameters $\underline{d} = \{d_1, d_2, \ldots, d_M\}$. Both the aforesaid parameter vectors are known with a margin of uncertainty.

The method may start processing from the model parameters and data, known a priori with a probability density $\rho(\underline{d},\underline{m}) = \rho_D(\underline{d}) \rho_M(\underline{m})$, which are used by a theoretical model $\Theta(\underline{d},\underline{m})$.

The data σ are obtained a posteriori as a function of the a priori data ρ, of the model state Θ and of their homogenous distribution μ:

$$\sigma(\underline{d}, \underline{m}) = k \frac{\rho(\underline{d}, \underline{m})\Theta(\underline{d}, \underline{m})}{\mu(\underline{d}, \underline{m})},$$

and the a posteriori probability density of the model, integrated in the data space, may be written as:

$$\sigma_M(\underline{m}) = \int_D \frac{\rho(\underline{d}, \underline{m})\Theta(\underline{d}, \underline{m})}{\mu(\underline{d}, \underline{m})} d\underline{d}$$

the formula being applied to the acoustic model to allow a particularly effective convergence, generally limited to a few iteration cycles. The Applicant has found that this formula allows to obtain a method which can be executed by a relatively simple hardware system and on the other hand is compatible with the required accuracy requirements of the calculation and with the production processes of the launching operations.

The steps of the method listed above are indicated below in greater detail. In the embodiment shown here, the anomaly detection algorithm firstly provides for choosing the range of distances to be analyzed; then, defining the analysis waveform (source) and further registering the ambient noise used for a possible shaping of the input acoustic signal to be emitted. The method then provides for emitting an analysis waveform and simultaneously registering it, and thus registering the echoes (acoustic return signal) from the pipeline. So, the next method step provides for identifying the defects, which is achieved by means of the following further steps.

The propagation of the analysis waveform is theoretically determined according to the theoretical model (the pipeline/fluid system features being known, such as diameter, thermodynamic properties of the air and so on) at increasing distances along the entire range of analysis distances. Then, the theoretically propagated waveform is compared, by means of cross-correlation, with the acoustic return signal (i.e. according to the second electric measurement signal) registered in the time window corresponding to the same distance. The result of such a cross-correlation is a reflection index along the pipeline having an amplitude proportional to a possible section reduction; a threshold criteria thus identifies the presence and the position of the defects.

According to the above, a time portion of the acoustic return signal is extracted containing the wave reflected by the defect, i.e. the observed datum, in a surround of the identified defect positions. So an iterative inversion procedure is activated which compares the observed data with the calculated data in a pipeline model with a hypothesized defect: the residue between data and estimate of the estimated data variations with respect to the defect parameters (Jacobian) guides the updating of the model and iteration of the procedure until convergence. The estimated model at the last iteration step displays the geometric parameters of the real defect.

It is worth noting that the method shown above, in all the described embodiments, allows to identify/locate and quantify the geometric defects in a given family of defects defined a priori and also to identify further anomalies with high accuracy.

Indeed, in an embodiment, the method can also identify and locate obstructions and/or obstacles in the pipeline, such as objects fallen during the launch, total obstructions or partial obstructions of the pipeline.

According to another example of application, the method can recognize significant discontinuities of the properties of the contained liquid (e.g. the air/water contact surface).

According to a yet further embodiment, the method provides for the repeated execution of the localization procedure of defects and obstructions, in known successive times, and the consequent calculation of possible "movements" of the defects between successive measurements, comprising the speed of such movements. Thereby, the method allows to trace the movement of obstacles in the pipeline and the detection of a water source, and of the corresponding movements, possibly present within the pipeline.

Hereinafter, with reference to FIG. 6, some details are shown, all known per se, of the propagation channel modeling, on which the step of theoretically defining the acoustic wave propagation is based.

The pressure wave propagation P(x,t) in the pipeline generated by the input acoustic signal may be represented by the formula:

$$P(x, t) = P(0, t) * e^{-\alpha x} * e^{j2\pi f(t - x/c_f)}$$

where x is the distance from the acoustic transmission unit; α is the attenuation coefficient, which can be also expressed as:

$$\left(\frac{1}{PipeRadius}\right) * \sqrt{(\pi * f * \mu)/(\rho * SoundSpeed^2)} * \left((1 + (\gamma - 1)/\sqrt{Pr}\right)$$

$c_f$ is the phase speed, which can also be expressed as $$SoundSpeed \Big/ \left(1 + \propto * \frac{SoundSpeed}{2 * \pi * f}\right)$$

$\mu$ is the viscosity; $\rho$ is the density; Pr is the Prandtl number, i.e. $\mu*Cp/k$; Cp is the specific heat; k is the thermal conductivity; $\gamma$ is the ratio of the specific heats; "SoundSpeed" is the speed of sound; "PipeRadius" is the radius of the pipeline.

Considering that a geometric anomaly produces the partial reflection of the incident signal, the amplitude of the reflected part may be expressed as:

$$R = P_r/P_i = (S1 - S2)/(S1 + S2)$$

while the amplitude of the transmitted acoustic wave which continues to propagate in beyond the anomaly may be expressed as:

$$T = P_t/P_i = 2*S1/(S1 + S2)$$

where S1 is the area of the tube section and S2 is the area of the section at the geometric anomaly.

Figure 6:
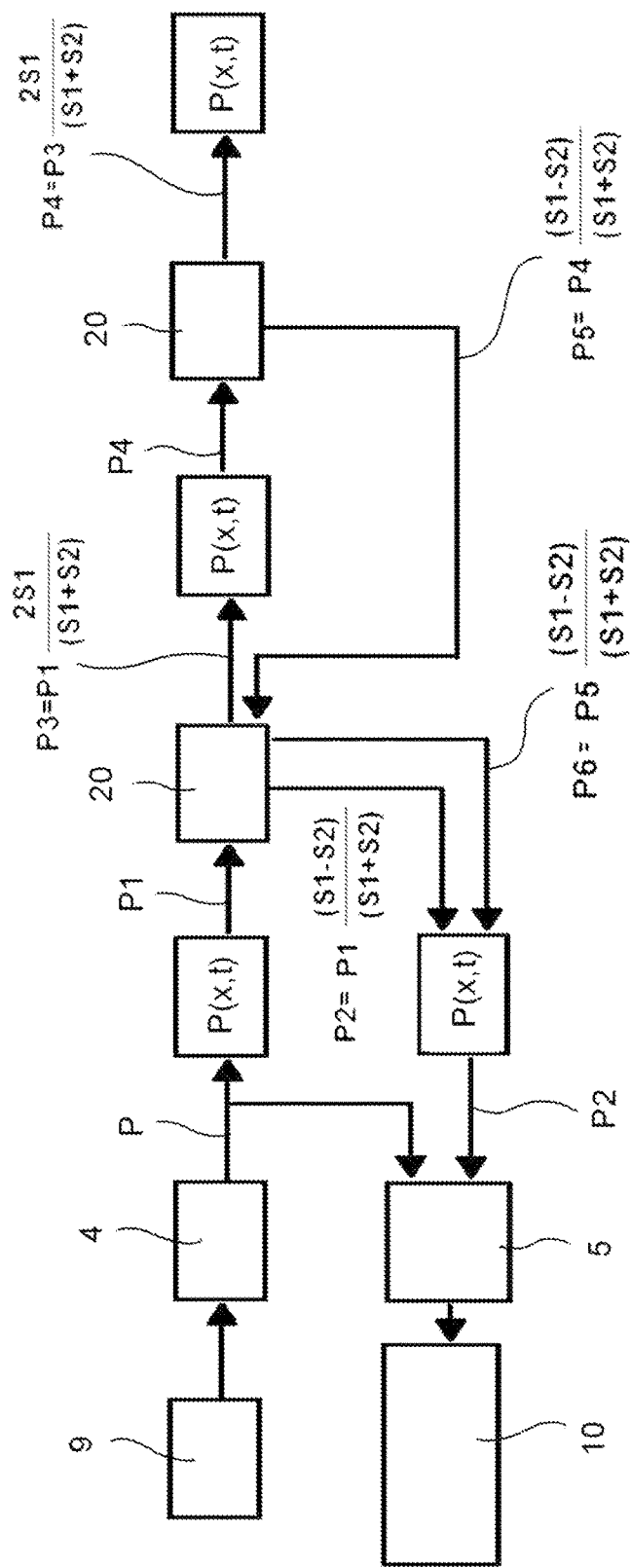
FIG. 6 shows a simplified diagram of a propagation and acoustic reflection model used in an embodiment of the method according to the invention.
Figure 7:
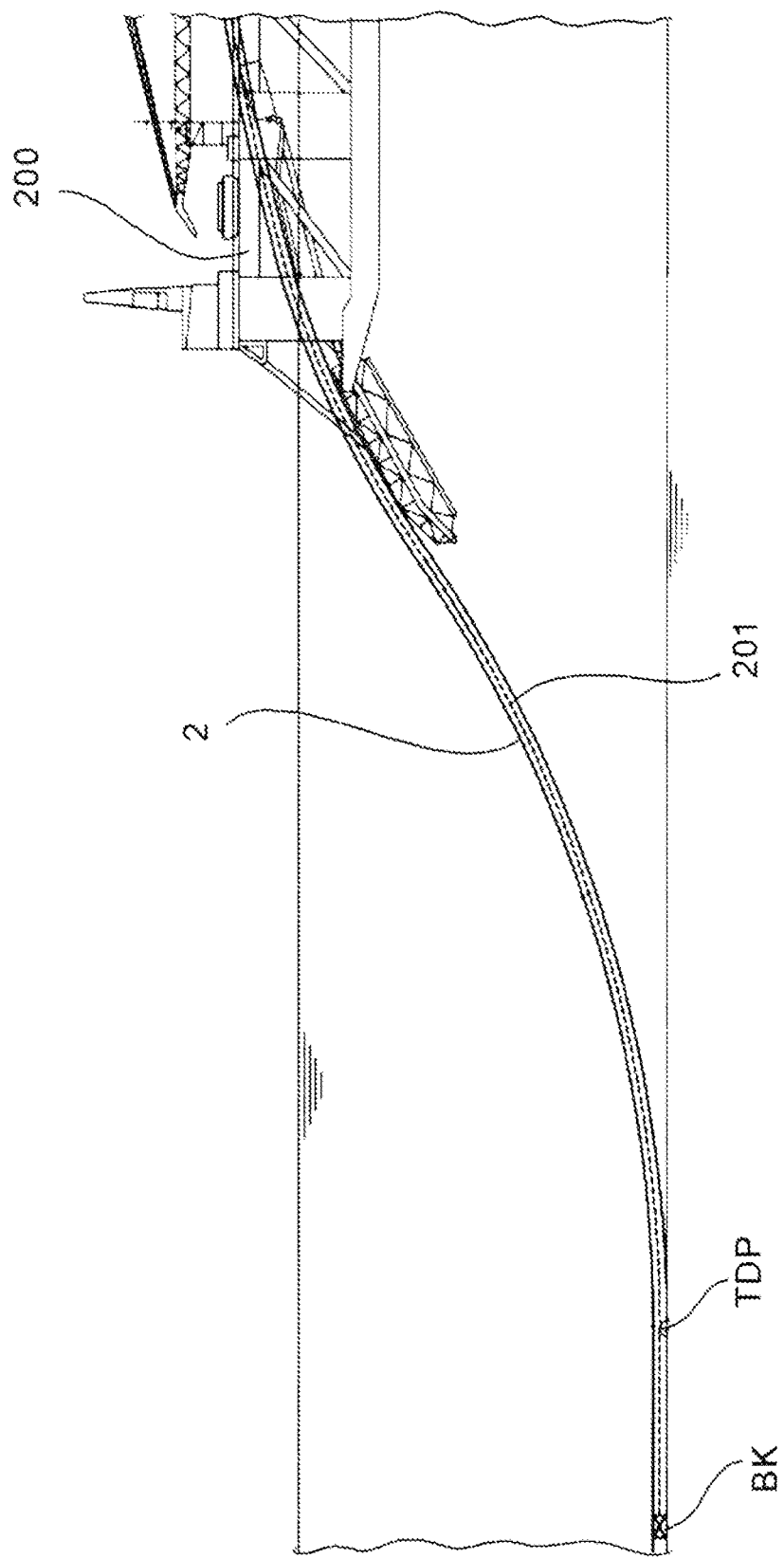
FIG. 7 diagrammatically shows a measuring technique belonging to the prior art, in the context of the launching of a pipeline on the seabed, by using a ship.
Figure 8C:
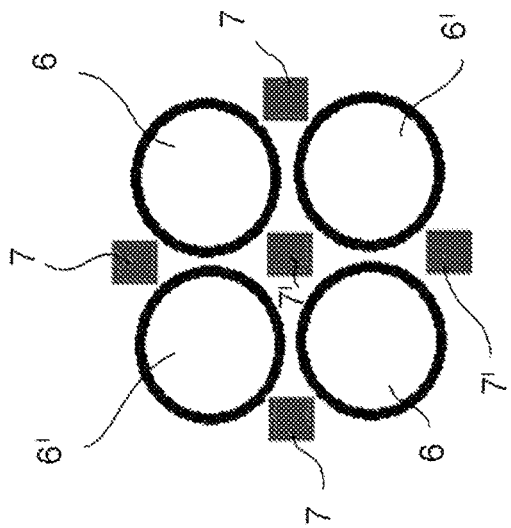
FIGS. 8a-8e diagrammatically show examples of arrangement of acoustic transmission elements and acoustic receiving elements provided in various embodiments of the system.
Figure 8B:
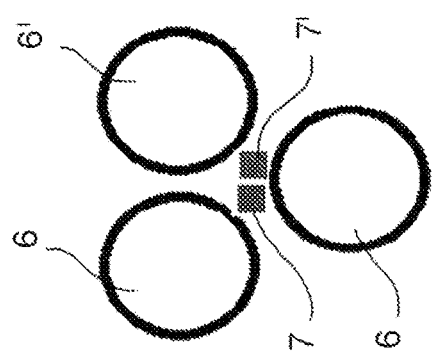
Figure 8E:
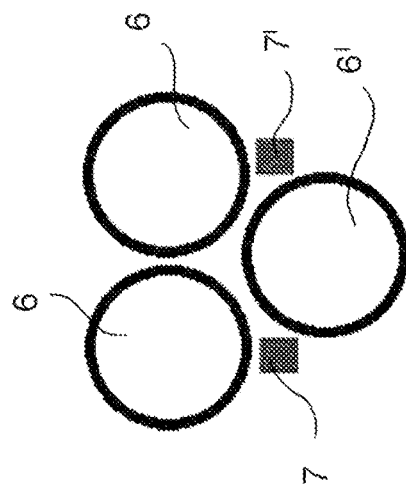
Figure 8A:
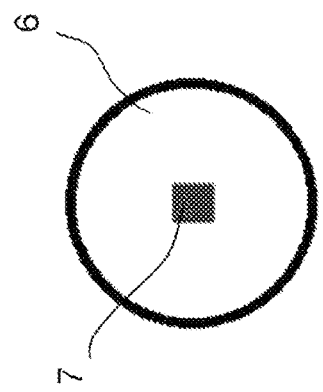
Figure 8D:
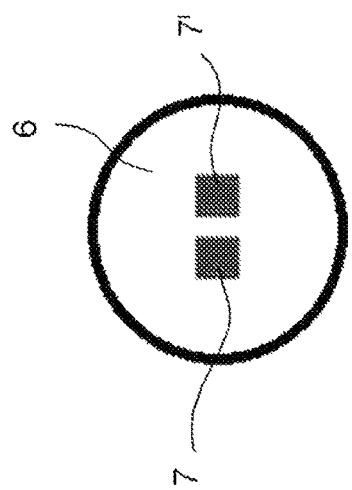

In FIG. 6, the input acoustic signal sa1 is indicated as a pressure wave P; the return acoustic signal sa2 is indicated as a pressure wave P2; the transmitted or reflected pressure waves, in the various sections of the pipeline, are indicated by references P1, P3, P4, P5, P6.

Now considering a discretization of the cylindrical pipeline sections 1, i−1, n, and considering an equivalent source which generates a monochromatic wave at section i, each successive section generates a transmitted wave (downward "d", rightwards) and a reflected wave (upward "u", leftwards), each of which is characterized by different reflection coefficients $R_i^d T_i^d R_i^u T_i^u$. The reflection coefficients may be calculated according to the sum of the single waves determined on the single section.

As can be observed, the objects of the invention are achieved by the system and method described above by virtue of the features shown above.

Indeed, the above-described system allows to use non-invasive techniques, which solves at the root all the previously mentioned drawbacks with reference to the invasive techniques (e.g. based on "buckle detectors").

Furthermore, the choice of using acoustic waves instead of electromagnetic waves (exploiting the fact that a pipeline can be a waveguide also for acoustic waves) allows to carry out monitoring measurements on wide distances, adapted to cover the pipeline stretches during laying in most of the possible real situations.

At the same time, the structural and functional features of the system allow to use the acoustic waves (input and return acoustic signals) so as to obtain considerable accuracy which is appropriate to the type of use.

In particular, the presence of an acoustic transmission unit and of an acoustic receiving unit which are mutually distinct allows to monitor both the acoustic return signal and the actual input acoustic signal accurately, which in turn allows to obtain measurements of accuracy adapted to needs.

It is worth noting that the signal processing carried out by the above-described present system advantageously allows to meet the further needs to detect the presence and also the type and position of the defects with great accuracy. Indeed, as described above, the system can execute algorithms based on a processing of the entire acoustic return signal (and in particular of all its spectrum components) and not only a measurement of the energy of such a signal.

Finally, by virtue of its structural and functional features, the system can detect "geometric" defects of the pipeline and, as described above, also the presence of possible obstacles in the pipeline, the movement of such obstacles and the presence of possible water in the pipeline.

Similar advantages can be identified with reference to the above-described methods employing the above system.

Furthermore, the field of application of the present invention further comprises the "reel" launching technique in addition to the "S-laying" and "J-laying" techniques.

Those skilled in art may make changes and adaptations to the embodiments of the above-described system for real time remote measurement, through sound waves, of geometric parameters of a pipeline in the launch step, and they can also replace elements with others which are functionally equivalent in order to meet contingent needs without departing from the scope of protection of the following claims. All the features described above as belonging to a possible embodiment may be implemented irrespective of the other embodiments described.

The invention claimed is:

1. System for real time remote measurement, through sound waves, of geometric parameters of a pipeline in a launch step, comprising an acoustic transceiver unit, positioned in the pipeline, and a control unit, wherein the acoustic transceiver unit comprises:
    an acoustic transmission unit configured to emit an input acoustic signal into the pipeline, based on an electric pilot signal, wherein said input acoustic signal comprises at least an acoustic pressure wave longitudinally propagating in a fluid along the pipeline;
    an acoustic receiving unit, distinct from the acoustic transmission unit, configured to detect and measure the input acoustic signal and to generate a first electric measurement signal, dependent on the input acoustic signal detected and measured, the acoustic receiving unit being configured to receive an input return signal, generated in the pipeline and dependent on the input acoustic signal and on the geometric parameters of the pipeline, and to generate a second electric measurement signal based on the return signal; and
    wherein the control unit is configured to generate the electric pilot signal and is operatively connected to the acoustic transceiver unit to provide the electric pilot signal and to receive the first electric measurement signal and the second electric measurement signal;
    the control unit being configured to measure the geometric parameters of the pipeline based on the first electric measurement signal and the second electric measurement signal.

2. System according to claim 1, wherein:
    the acoustic transmission unit comprises at least two acoustic transmission elements configured to emit an input acoustic signal comprising at least one mode of acoustic propagation;
    the acoustic receiving unit comprises at least two acoustic receiving elements configured to receive an acoustic signal comprising said at least one mode of acoustic propagation;

the control unit is configured to generate an electric pilot signal comprising one or more electric pilot signals suitable for controlling each of the at least two acoustic transmission elements.

3. System according to claim 2, wherein:
said at least two acoustic transmission elements are configured to emit an input acoustic signal comprising a fundamental mode of acoustic propagation and at least one further mode of acoustic propagation;
said at least two acoustic receiving elements are configured to receive an acoustic signal comprising at least said fundamental mode of acoustic propagation and at least one further mode of acoustic propagation.

4. System according to claim 2, wherein said at least two acoustic transmission elements are configured to respectively emit a first transmitted acoustic signal and a second transmitted acoustic signal, said first acoustic signal and said second acoustic signal acoustically combining to form the input acoustic signal.

5. System according to claim 2, wherein two acoustic transmission elements are controllable independently from each other, so that the first transmitted acoustic signal and the second transmitted acoustic signal are different from each other, to determine a plurality of possible input acoustic signals.

6. System according to claim 2, wherein:
each of said acoustic transmission units or acoustic transmission elements and each of said acoustic receiving units or acoustic receiving elements comprises an electro-acoustic transducer, and wherein the control unit comprises:
an acquisition unit of the first electric measurement signal and of the second electric measurement signal;
an electric pilot signal generating unit;
a processor, configured to carry out processing aimed at measuring the geometric parameters of the pipeline, based on said first and second electric measurement signal, and to control the electric pilot signal generating unit.

7. System according to claim 2, wherein:
said at least two acoustic transmission elements comprise a matrix of loudspeakers, arranged in predetermined positions;
said at least two acoustic receiving elements comprise a matrix of microphones arranged in predetermined positions.

8. System according to claim 1, wherein the control unit is configured to:
define an analysis waveform and generate the electric pilot signal so that the input acoustic signal is modulated through the analysis waveform;
define an expected propagation model;
estimate an ideal acoustic return signal, based on the analysis waveform and the expected propagation model;
carry out a comparison between the estimated ideal acoustic return signal, within a time window, and the acoustic return signal detected based on the second electric measurement signal, within a corresponding time window;
obtain the geometric parameters of the pipeline, based on said comparison, the geometric parameters obtained being representative of a shape actually detected of the pipeline and of anomalies and/or defects found.

9. System according to claim 8, wherein the control unit is configured to define the analysis waveform based on a desired range of distances within which to detect defects, and/or based on a type of defects to be detected and/or based on an expected defect.

10. System according to claim 8, further comprising means for detecting background noise, and wherein the control unit is configured to define the analysis waveform taking into account background noise detected.

11. System according to claim 8, wherein the control unit is configured to generate the analysis waveform as a sinusoidal waveform modulated in frequency through "chirp" and/or modulated in amplitude and/or as a Ricker type wave or a Klauder type wave or an Ormsby type wave.

12. System according to claim 8, wherein the control unit is configured to define the expected propagation model based on geometric parameters of a geometric model of the pipeline in the absence of laying anomalies.

13. System according to claim 12, wherein the control unit is configured to define the expected propagation model also taking into account thermodynamic parameters of the fluid contained in the pipeline.

14. System according to claim 8, wherein the control unit is configured to estimate the ideal acoustic return signal and to detect the acoustic return signal based on said first and second electric measurement signal.

15. System according to claim 8, wherein the control unit is configured to carry out said comparison through a cross-correlation between the estimated ideal acoustic return signal, within a time window, and the detected acoustic return signal, within a corresponding time window.

16. System according to claim 7, wherein the control unit is configured to carry out the following operations:
determining, based on comparison between the estimated ideal acoustic return signal and the detected acoustic return signal, a spatial reflection function of the pipeline, representative of reductions in diameter of the pipeline as a function of the distance;
identifying presence and spatial position of defects based on said spatial reflection function;
defining an estimated real geometric model of the pipeline, having an estimated defect at the defect position identified;
calculating an expected acoustic return signal, based on the estimated real geometric model of the pipeline;
modifying geometric parameters of the estimated real geometric model of the pipeline, based on a cross-correlation between the expected acoustic return signal and the detected acoustic return signal, within a time window corresponding to the position around the defect identified;
repeating said modification process until a convergence of the geometric parameters is achieved, to obtain a real geometric model of the pipeline representative of the detected shape of the pipeline and of the anomalies found.

17. System according to claim 1, further comprising means for detecting ambient pressure configured to supply the control unit with information representative of the ambient pressure detected.

18. System according to claim 1, wherein the control unit is configured to store temperature information and/or temperature profiles present or expected along the pipeline.

19. System according to claim 8, wherein the control unit is configured to define the expected propagation model taking into account said ambient pressure and/or temperature information.

20. System according to claim 1, wherein the control unit is configured to store a plurality of measurements of geometric parameters and estimate, based on said plurality of measurements, a spatial-temporal evolution of one or more sections of the pipeline.

21. System according to claim 1, further comprising means for estimating the shape of the pipeline in the launch step and before laying, configured to measure cross sections of portions of pipeline in the launch step and to provide the control unit with information representative of the shape of the pipeline in the launch step and before laying, based on the cross sections progressively measured, and
wherein the control unit is configured to measure the geometric parameters of the pipeline taking into account said information representative of the shape of the pipeline in the launch step and still aboard a pipeline-laying naval vessel.

22. System according to claim 1, wherein:
the acoustic transceiver unit is mechanically integrated in an inner clamp of a laying apparatus adapted to manage coupling and welding of portions of pipe in the launch step;
the control unit is arranged remotely with respect to the acoustic transceiver unit,
the system further comprising communication means between the acoustic transceiver unit and the control unit.

23. Method for real time remote measurement, through sound waves, of geometric parameters of a pipeline in the launch step, comprising the steps of:
emitting into the pipeline, by an acoustic transmission unit, an input acoustic signal, based on an electric pilot signal, wherein said input acoustic signal comprises at least an acoustic pressure wave longitudinally propagating in a fluid along the pipeline;
detecting and measuring said input acoustic signal, by an acoustic receiving unit, distinct from the acoustic transmission unit, and generating a first electric measurement signal, dependent on the input acoustic signal detected and measured;
receiving, by the acoustic receiving unit, a return acoustic signal, generated in the pipeline and dependent on the input acoustic signal and on the geometric parameters of the pipeline, and generating a second electric measurement signal based on the return acoustic signal;
measuring the geometric parameters of the pipeline, by a control unit, based on the first electric measurement signal and the second electric measurement signal.

24. Method according to claim 23, wherein the step of emitting an input acoustic signal comprises respectively emitting a first transmitted acoustic signal, by a first element of the acoustic transmission unit, and a second transmitted acoustic signal, by a second element of the acoustic transmission unit, wherein the first transmitted acoustic signal and the second transmitted acoustic signal combine to form the input acoustic signal.

25. Method according to claim 23, comprising the further steps of:
defining an analysis waveform and generating the electric pilot signal so that the input acoustic signal is modulated through the analysis waveform;
defining an expected propagation model;
estimating an ideal acoustic return signal, based on the analysis waveform and the expected propagation model;
carrying out a comparison between the estimated ideal acoustic return signal, within a time window, and the return acoustic signal detected based on the second electric measurement signal, within a corresponding time window,
obtaining the geometric parameters of the pipeline, based on said comparison, the geometric parameters obtained being representative of a shape detected of the pipeline and of anomalies and/or defects found.

26. Method according to claim 25, wherein the step of defining the analysis waveform comprises defining the analysis waveform based on a desired range of distances within which to detect defects, and/or based on a type of defects to be detected and/or based on an expected defect.

27. Method according to claim 25 further comprising the steps of:
detecting background noise;
defining the analysis waveform taking into account the detected background noise.

28. Method according to claim 25, wherein the step of generating the analysis waveform comprises generating a sinusoidal waveform modulated in frequency through "chirp" and/or modulated in amplitude and/or as a Ricker type wave or a Klauder type wave or an Ormsby type wave.

29. Method according to claim 25, wherein the step of defining the expected propagation model based on geometric parameters of a geometric model of the pipeline without laying anomalies and/or on thermodynamic parameters of the fluid contained in the pipeline.

30. Method according to claim 25, wherein the step of carrying out a comparison comprises carrying out a cross-correlation between the estimated ideal acoustic return signal, within a time window, and the detected acoustic return signal, within a corresponding time window.

31. Method according to claim 30, wherein the step of obtaining the geometric parameters of the pipeline comprises:
determining, based on the comparison between the estimated ideal acoustic return signal and the detected acoustic return signal, a spatial reflection function of the pipeline, representative of reductions in diameter of the pipeline as a function of the distance;
identifying presence and spatial position of defects based on said spatial reflection function;
defining an estimated real geometric model of the pipeline, having an estimated defect at the defect position identified;
calculating an expected acoustic return signal, based on the estimated real geometric model of the pipeline;
modifying geometric parameters of the estimated real geometric model of the pipeline, based on a cross-correlation between the expected acoustic return signal and the detected acoustic return signal, within a time window corresponding to the position around the defect identified;
repeating said modification process until a convergence of the geometric parameters is achieved, to obtain a real geometric model of the pipeline representative of the detected shape of the pipeline and of the anomalies found.

32. Method according to claim 25, suitable for measuring parameters relative to any combination of the following anomalies:
geometric defects; dents; variations in section diameter; variations in section shape; blockages and/or obstacles present in the pipeline; significant discontinuities of the properties of the fluid contained in the pipeline; displacement of objects and/or defects in the pipeline between successive measurements; presence of water in the pipeline.

\* \* \* \* \*